United States Patent
Kumar et al.

(10) Patent No.: US 7,262,003 B2
(45) Date of Patent: Aug. 28, 2007

(54) PLANT TEST PROCEDURE TO DETECT NATURAL, SEMI-SYNTHETIC, SYNTHETIC COMPOUNDS AND PHYSICAL STRESS FACTORS THROUGH EXPRESSION OF DISTINCT RESPONSES

(75) Inventors: Sushil Kumar, Lucknow (IN); Suman Preet Singh Khanuja, Ulan Pradesh (IN); Mahendra Pandurang Darokar, Ulan Pradesh (IN); Tiruppadiripuliyur Ranganathan Santha Kumar, Ulan Pradesh (IN); Anita Gangwar, Ulan Pradesh (IN); Ajit Kumar Shasany, Lucknow (IN); Srilekha Mishra, Ulan Pradesh (IN); Shalini Mathur, Ulan Pradesh (IN); Dharmendra Saikia, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 582 days.

(21) Appl. No.: 10/319,111

(22) Filed: Dec. 13, 2002

(65) Prior Publication Data

US 2004/0029098 A1 Feb. 12, 2004

Related U.S. Application Data

(63) Continuation-in-part of application No. 09/246,862, filed on Feb. 8, 1999, now abandoned.

(30) Foreign Application Priority Data

Dec. 9, 1998 (IN) .............................. 3704/DEL/98

(51) Int. Cl.
*C12Q 1/00* (2006.01)
(52) U.S. Cl. .......................................... 435/4
(58) Field of Classification Search .................... 435/4, 435/420; 514/1
See application file for complete search history.

(56) References Cited

U.S. PATENT DOCUMENTS 5,477,000 A 12/1995 Saxena et al.

OTHER PUBLICATIONS

Ali et al, 1996, Plant Tiss. Cult. Biotech. 2:208-211.*
Webster's Unabridged Dictionary of the English Language, 2001, Random House, New York, p. 364.*
Thakur, et al; Department of Botany, University of Delhi/India; "In Vitro Shoot Bud Differentiation from Epidermal Cells of Stem Segments in *Bacopa monnieri* (Linn.) Pennell" Beitrage zur Biologie der Pflanzen; 21 Beitr. Biol. Pflanzen 53, 321-330 (1977); Duncker & Humblot, Berlin.
D. Philcox; "Clarification of the name *Bacopa monnieri* (Scrophulariaceae)"; Kew Bulletin vol. 33(4); p. 679-680; provided by the University of Washington Libraries, US.
Gayoor, et al; "A Rapid Protocol for Micropropagation of *Bacopa monniera* (L.) Wettst.—an Important Medicinal Plant"; Plant Tissue Culture and Biotechnology, Dec. 1996, vol. 2, No. 4; p. 208-211; US.
Gayoor, et al; "Morphogenic Response and Isozymes and *Bacopa monniera* (L.) Wettst Cultures Grown Under Salt Stress"; Phytomorphology, (1997) vol. 47, No. 1; pp. 97-106.
Gayoor, et al; "Morphogenic Response and Proline Content in *Bacopa monniera* Cultures Grown under Copper Stress"; Plant Science 138 (1998) 191-195; Elsevier Science Ireland Ltd.
Ali, et al.; "Aluminium-Induced Morphogenic and Biochemical Variations of *Bacopa monniera*" J. Plant Biol. 41(3):240-245 (1998).
Tiwari, et al.; "Shoot Regeneration and Somatic Embryogenesis from Different Explants of Brahmi [*Bacopa monniera* (L.) Wettst. ]"; Plant Cell Reports (1998) 17: 538-543.
Ali, et al; "Effect of Cadmium and Copper on Growth of *Bacopa monniera* regenerants"; Biologia Plantarium 41 (4): 6356-639, 1998.
Biasi, L.A.; "Phytotoxicity of Three Antibiotics to Avocado Tissue Culture"; Bragantia, (1995) vol. 54, No. 2; pp. 251-256. 23 ref. ISSN: 0006-8705; Departmento de Horticultura, Brazil.

* cited by examiner

*Primary Examiner*—Anne Kubelik
(74) *Attorney, Agent, or Firm*—Ross Spencer Garsson; Mark Solomon; Winstead Sechrest & Minick P.C.

(57) ABSTRACT

The present invention relates to a method of testing *Bacopa monnieri* response to abiotic stress factors and for testing bioactivity of natural, synthetic and semisynthetic compounds using *Bacopa monnieri* plant, which comprises growing the said plant and plant parts aseptically in MS 0 basal medium with agar in microcentrifuge tubes by adding the compounds to be tested either to the culture media or by spraying the said compounds on the plant or plant parts or on the said medium to detect the distinct morphological and cytological responses.

21 Claims, 2 Drawing Sheets

PLANT TEST PROCEDURE TO DETECT NATURAL, SEMI-SYNTHETIC, SYNTHETIC COMPOUNDS AND PHYSICAL STRESS FACTORS THROUGH EXPRESSION OF DISTINCT RESPONSES

CROSS REFERENCE TO RELATED PATENTS

This application for patent is a continuation in part of the following applications for patent:

U.S. patent application Ser. No. 09/246,862, filed Feb. 8, 1999 now abandoned by inventors Kumar, et al. entitled "Novel Plant Test Procedure to Detect Natural Semi-Synthetic Compounds and Physical Stress Factors Through Expression of Distinct Responses" which claimed priority to Application Serial No. 3704/DEL/98, filed with the Indian Patent Office on Dec. 9, 1998.

FIELD OF THE INVENTION

The present invention relates to a method for testing bioactivity of the natural, synthetic, semisynthetic compounds and monitoring exposure to abiotic stress factors using *Bacopa monnieri* plant. More particularly, the invention relates to a method for novel plant test expression system using a rapid propagating *Bacopa monnieri* plant capable of detecting natural or synthetic compounds useful in promoting or inhibiting plant growth and other activities like cell division, cytotoxic, weedicidal and anticancerous activities and also as a biosensor for monitoring the physical stress factors and hazards in the environment including ionizing, and non ionizing radiation (radioactivity), heat and cold shocks.

BACKGROUND

Bioactivity testing for the chemical compounds whether natural, semisynthetic or synthetic and monitoring environment for the presence of physical stress factors and hazards like radioactivity, radiation and temperature shocks have been a major concern for all those who are concerned about the environment for the following main reasons:

Monitoring the compounds for their toxicity or pollution hazards before they are permitted to be released into any practical use in the environment.

Bioevaluating the compounds for their potentials in developing drugs or agrochemicals Biosensing the presence of physical extremities in the environment which could amount to physical damage/shock to the organisms living there.

The emphasis in the present day scenario is centered on natural compounds not only for their direct use but also for providing the biorational leads in developing semisynthetic compounds with higher efficacy. These biorational leads are expected to be more biocompatible and therefore the appropriate tests have to be applied for both positive and negative effects. About 51 tests are well known to be approved for the use within OECD countries (Organization for Economic Co-operation and Development: Guidelines for Testing of Chemicals. OECD, Paris, 1981, for testing of chemical compounds. Some of the higher plant species have also been used for toxicity assessment of industrial wastewater including common duckweed (*Lemna minor*), lettuce, rice (*Oryza sativa*) and wheat etc. Wang W, 1990, Res. J. Water Pollut. Con. Fed. 62: 853–860; Wang W, 1991, Plants for Toxicity Assessment, second volume, J W Gorsuch, W R Lower, W Wang and M A Lewis, Eds. ASTM STP 1115, American Society for Testing and Materials, Philadelphia, pp 68–70). A single test has never been advocated as sufficient enough to be employed as biotesting procedure particularly, when the compound under question is to be evaluated for environmental toxicity/hazard (Fiskesjo G, 1982, Ph.D. Thesis, Institute of Genetics, University of Lund, Sweden).

In addition, use of a battery of tests rather than any single test in isolation has also been preferred to reduce the possibility of false negative and false positive results (de Serres, 1976, Mutation Research, 38: 165–176 and 355–358). In fact, this opinion has always been the general consensus among the regulatory agencies as well (Committee 17, 1975, Science, 187:503–514). Availability of several tests has resulted into their broad classification among four main classes (Maugh, 1978 Science, 201:1200–1205). These include:

The tests with micro-organisms.
The tests with intact organisms.
The tests with cultured/mammalian cells.
The tests for in-vitro activities.

In the above categories, for the tests with intact organism, a very popular root tip assay system using *Alliuin ceua* sprouted bulbs was introduced by Levan 1938, while investigating the effects of colchioine. The usefulness of plant system in tests of chemicals even those which need metabolic activation has been emphasized (Vig B K, 1978, Environment Health Perspect. 27: 27–36) for the preliminary screening of new chemicals being introduced into the environment. The Allium test has also been listed as a short term procedure for the detection of chemical carcinogens (Stich H F, 1975, Can. J. Genet. Cytol. 17:471–492). The positive results in these tests have been suggested to be considered as a warning that the tested chemicals may be a risk to human health. The first attempt to approach the problem of genotoxical effect of environmental chemicals was on a commercial fungicide (called Be Toxin) containing mercury compounds (Levan A, 1945, Nature, 156:751). Subsequent studies on effect of mercury halogenides in Allium tests have substantiated the confirmation with compounds like methyl mercury chloride (MMC) and ethyl mercury chloride (EMC) etc. (Levan A, 195 1, C.S.H. Symp. Quant. Biol. 16:233–243; Fahmy F Y, 1951, Ph.D. thesis, Inst.Genet., Lund, Sweden; and Remel, C. 1969, Hereditas 61:208–230). The original form of test wherein outgrowth of root tips from onion bulbs in fresh water which was followed by treatment with test chemical solution has undergone several modifications to have several replicates together (Fiskesjo G, 1975, Vatten 31(4):304–316 and Fiskesjo G, 1981, Vatten 37(3):232–240).

The system, although very useful to study the responses of a variety of cell division inhibiting substances, has certain inbuilt limitations which are as follows:

The parameters which can be studied using this test procedure are mainly confined to cytological observations including cell division.

This test is not usable for assessing the growth promotion activities since the responses are observed only in the root tips and thus do not take into consideration the effects on aerial parts of the plant as a direct measure.

It requires independent onion bulbs in the sprouting stage for each treatment of every replication which amounts to large bulk of starting material and becomes impractical when thousands of samples are to be tested.

The root sprouting of bulbs is not possible throughout the year under ambient condition and therefore the experiment would require storing the right stage of bulb under controlled conditions.

Each bulb has to be sprouted on top of a tube/flask filled with buffer having minimum 15×20 mm diameter and therefore requires large volumes of buffer or medium for testing the compounds.

OBJECTS OF THE INVENTION

The object of the invention is to use the rapid growing herb *Bacopa monnieri* in the bioassay procedures for detecting distinct plant response in the presence of test compounds and extracts in a convenient, rapid and repetitive manner. The experiments were specifically designed to analyze the use of procedures based on the observations and interpretations of the Bacopa test which is unique and efficient for its multi-purpose applications, providing a suitable alternative for not only traditional root tip assays (Allium test) and shoot growth assays (coleoptile procedure) but also having its applicability in assessing chemical compounds with cytotoxic or weedicidal effects. Another object of the invention is to provide an unique process to monitor various elements of environmental pollution.

DETAILED DESCRIPTION OF THE INVENTION

The present invention provides a novel test process by utilizing a fast growing plant *Bacopa monnieri*. The effects of natural, semisynthetic and synthetic compounds, and physical stress factors on the living system can be tested in a rapid and much simpler way. The chemical compounds whose effects can be tested by this process are growth promoters, growth inhibitors, cytotoxic and weedicidal compounds, cell division inhibitors and antimitotic/anticancerous compounds. The effects of physical factors like temperature, ultra violet, and gamma irradiation on living systems can be tested using this process. The novel process is important as it can be used as a biosensor in the present world of environmental pollutants and biohazards.

The invention of this test procedure is a consequence of planned experiments carried out for developing a simple, repeatable, and rapid procedure using plants or plant parts to detect the biological activities of various natural and synthetic compounds.

The Applicants initiated the experiment to search for a better plant system which is available in plenty, grows rapidly, propagates vegetatively, and can show rooting response with aerial parts to test the effect of pollutants on living systems. One such plant *Bacopa monnieri* (family: Scrophulariacea), which is used at CIMAP in experiments for medicinal values, was found to be responding very fast for all type of explants under culture conditions. This plant is a small prostrate herb with ascending branching and grows wildly throughout the plains of India, including the coastal region. Therefore, from the point of view of availability of plant material as well as its quick response under controlled conditions, it was tested for specific responses to develop a procedure of biotesting the natural and synthetic compounds as well as biosensing the environment for physical stress factors. While developing the plant test system the drawbacks of the other system were kept in mind. As mentioned earlier, the Applicants used the rapid growing herb *Bacopa monnieri* in the bioassay procedures for distinct responses in the presence of test compounds and extracts in a convenient, rapid and repeatable way. The experiments were specifically carried out to analyze the use of procedures based on the observations and interpretations about the Bacopa test being unique and efficient for its multi-purpose applications, providing better alternative to not only the traditional root tip assays (Allium tested) and shoot growth assays (coleoptile procedure) but also its applicability in assessing chemical compounds with cytotoxic or weedicidal effects.

Initially the experiments were designed to observe the response of leaf, internode and cuttings against growth promoters (auxins: 2,4-D & Indole acetic acid) and growth inhibitors (cytokinins: 6-Benzyl amino purine & kinetin). The basal medium for studying the response was MS 0 (Murashige T and Skoog F, 1962, Physiol. Planta. 15: 473–497) supplemented with these growth regulators at the rates of 0.5 and 1.0 mg/litre along with a control of just the basal medium. In the case of leaf explant, as well as internodal parts, profuse rooting was observed for Indole acetic acid, while in the case of 2,4-D small thick roots got initiated at the internodes. For BAP, green callus developed in all three explants followed by shoot regeneration. In control experiment, root initiation occurred from leaves and cuttings but was conspicuously delayed by 4–6 days.

Another set of experiments was conducted to ascertain whether the initiated roots or even the root initiation process itself could be used as a parameter for cell division inhibition studies to compare its use as a system to replace the Allium test (Fiskesjo G. 1975, Vatten 31(4):304–316). Since plant growth in a single pot can yield thousands of twig cuttings and each cutting could be used as the starting material for root initiation as well as the root tip assays it becomes an advantage for large scale rapid monitoring of the cell division inhibition. In these experiments, various concentrations of taxol ranging from 1 to 100 µg/ml were taken. The roots were initiated from large number of cuttings in the basal medium by culturing for one week. For root tip assays the twigs with initiated roots were dipped in basal medium broth containing different levels of taxol and related compounds for different time intervals followed by fixation, staining in heamatoxylin for two hours and mounting on slides followed by observation for mitotically dividing cells. For root initiation assays, on the other hand, the fresh twigs were directly planted into 1.5 ml microcentrifuge tube containing basal medium plus taxol at various concentrations. In the case of root initiation assays, it was observed that the twigs did not initiate the roots at all even after 14 days and there was no shoot growth as well. Rather, wilting and later withering was observed in treated samples. In the case of a root tip assay with taxol, a substantial reduction in the mitotic index was observed for taxol at the rate of 10 µg/ml. The observed mitotic index showed 2.55 fold reduction compared to untreated control samples. Taxol at the rate of 100 µg/ml inhibited almost complete cell division in the root tips.

For studying the response of Bacopa twigs as a biosensor system against physical factors, tests were conducted to see the effect of temperature shock and radiation exposure. It was observed that temperatures between 0 to D° C. caused early root initiation, while temperature shock of −20° C. beyond 10 min caused the death of plantlets. In the case of higher temperature shocks the plants died upon a shock of more than 1 min at 50° C. or more than 20 seconds at 80° C. In UV exposure experiments the twigs could tolerate UV radiation up to 2 hrs but beyond this time the survival was drastically affected and after 8 hrs 100% mortality was observed.

Accordingly, the invention provides a novel process wherein a method for testing abiotic stress factors and bioactivity of the natural, synthetic and semisynthetic compounds *Bacopa monnieri* plant, which comprises growing the said plant and plant parts aseptically in MS basal medium with agar in microcentrifuge tubes by adding the compounds to be tested either to the culture media or by spraying the said compounds on the plant or plant parts or on the said medium to detect the distinct morphological and cytological responses.

In one embodiment, the compounds to be tested are used either in pure or crude extract form.

In another embodiment, the morphological responses to be detected are selected from the group consisting of callus initiation, shoot induction, root induction, necrosis and death.

In yet another embodiment, the cytological responses to be detected are selected from the group consisting of mitotic index and C-mitosis.

In yet another embodiment, the compounds used for bio-testing includes growth promoters selected from the group consisting of auxins and cytokinins.

In yet another embodiment, the auxins used are selected from the group consisting of, but not limited to, Indole-3-acetic acid 2,4-Dichlorophenoxy acetic acid.

In yet another embodiment, the cytokinins used are selected from the group consisting of, but not limited to, 6-Benzyl amino purine and kinetin.

In another embodiment, the compounds used for bio-testing comprises growth inhibitors are selected from the group consisting of nalidixic acid and abscisic acid.

In another embodiment, the compounds used for bio-testing include weedicidal compounds.

In yet another embodiment, the weedicidal compound used, is but not limited to, 2,4-Dichlorophenoxy acetic acid.

In other embodiment, the compounds used for bio-testing include antimitotic and anticancerous compounds.

In another embodiment, the antimitotic and anticancerous compounds are selected from the group consisting of, but not limited to, taxol, trichothecene, vincristine, vinblastine and nalidixic acid.

In further embodiment, the compounds used for bio-testing include cytotoxic compounds.

In yet another embodiment, the cytotoxic compounds are selected from the group consisting of, but not limited to, menthol, mint oil, artemisia oil, basil oil and essential oil components.

In yet another embodiment, the abiotic stress factors used are selected from the group consisting of radiations, Ultra violet rays, gamma rays, radioactivity, heat shock and cold shock conditions in the environment.

In another embodiment, the bioactivity of growth promoter compounds is detected by profuse root initiation, root thickening, callusing and regeneration during a period ranging between 7 to 15 days.

In yet another embodiment, the bio-activity of growth inhibiting compounds is detected by absence of root initiation, wilting and/or withering within 2 weeks.

In yet another embodiment, the bioactivity of weedicidal compounds is detected by necrosis and death of the explant within a period of 3 days.

Further, in another embodiment, the bioactivity of antimitotic and anticancerous compounds is detected by reduction in cell division and miotic index within 7 days.

Further, in yet another embodiment, the bioactivity of cytotoxic compounds is detected by complete loss of chlorophyll within 3 days.

In another embodiment, the response to abiotic stress factors is detected by lethality after treating for 2 hours or more with the UV radiation within a period of 15 days.

In yet another embodiment, the response to abiotic stress factors is detected by absence of shoot proliferation and reduction in elongation and rooting, and increase in lethality at a dose greater than 5 Kr gamma radiation within a period of 15 days.

In yet another embodiment, the response to abiotic stress factors is detected by temperature sensitivity of *Bacopa monnieri* plants at a temperature of 80° C. for 20 seconds or more within a period of 7 days.

In yet another embodiment, response to abiotic stress factors is detected by temperature sensitivity of *Bacopa monnieri* plants at a temperature of 50° C. for 3 min or more within a period of 7 days.

In another embodiment, the response to abiotic stress factors is detected by temperature sensitivity of *Bacopa monnieri* plants at a temperature of −80° C. for 4 min or more within a period of 7 days.

In yet another embodiment, the response to abiotic stress factors is detected by temperature sensitivity of *Bacopa monnieri* plants at a temperature of −20° C. for 10 min or more within a period of 7 days.

In the other embodiment, the method tests abiotic stress factors and bioactivity of the natural, synthetic, semisynthetic compounds using *Bacopa monnieri* plant substantially as herein described and illustrated with reference to examples and Figures.

BRIEF DESCRIPTION OF THE ACCOMPANYING DRAWINGS

DESCRIPTION OF THE INVENTION

Figure 1:
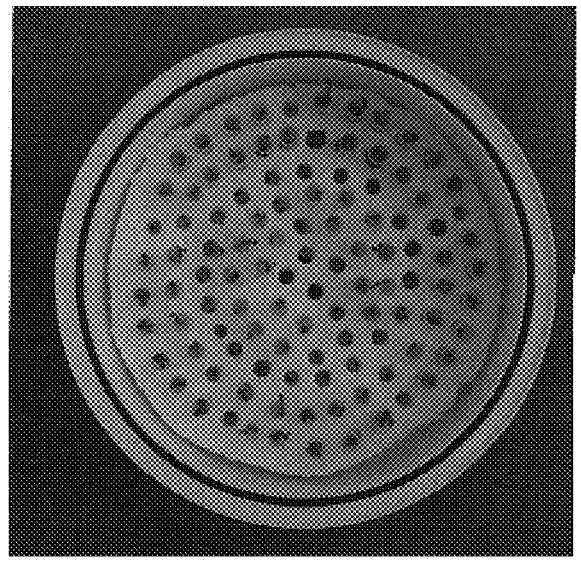
FIG. 1 shows inoculated tubes in a half-transparent box.
Figure 2:
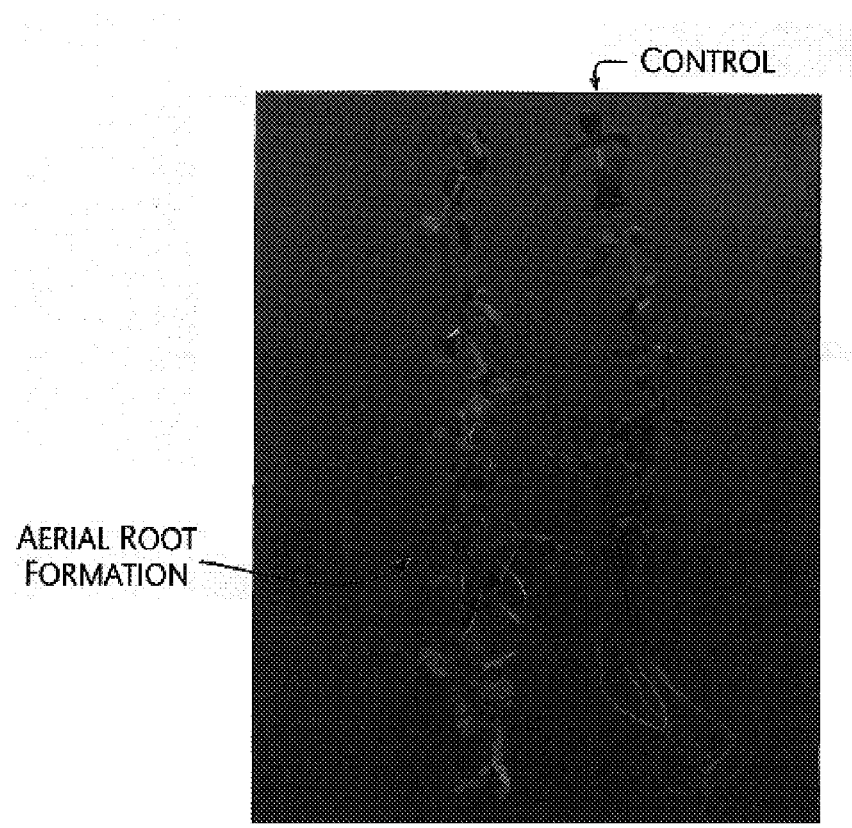
FIG. 2 shows aerial root formation in the case of cuttings upon auxin treatment.
Figure 3:
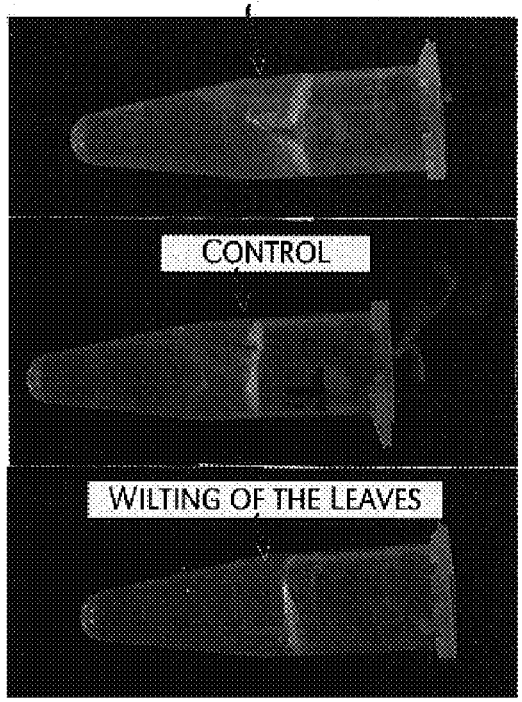
FIG. 3 shows inhibition of root initiation and effect on aerial parts in terms of wilting of leaves.
Figure 4:
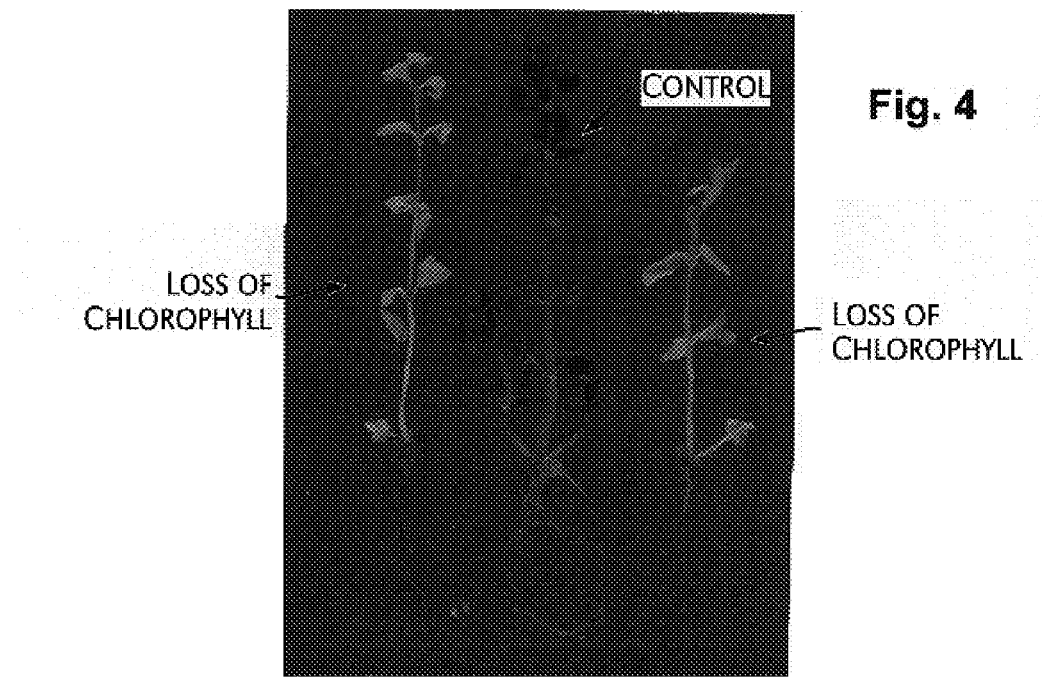
FIG. 4 shows loss of chlorophyll in lower leaves of the twig

In order to use Bacopa plant/plant parts for root initiation and shoot elongation, it is mandatory that the conditions should be standardized for efficient root initiation and elongation. The basal medium for studying the response was MS 0 (Murashige T and Skoog F, 1962, Physiol. Planta. 15: 473–497) supplemented with test compounds along with a control of just the basal medium. Measured 0.5 ml medium was poured into 1.5 ml graduated microcentrifuge tubes. Into this, twig cutting of 2.5 cm were inoculated in 20 replicates for each type of medium. These inoculated tubes were put into a half transparent (top lid) box allowing air passage through sterile cotton plugs such that the medium containing portion of the tubes where roots would be initiating is inserted into the stand holes made from a thermocol sheet. Refer FIG. 1 of Sheet #1. This set up was helpful in preventing the light exposure to the root portion while at the same time aerial parts got sufficient light and aeration. Such boxes were incubated at normal ambient temperature of 25–28° C. with 14 hours light and 10 hours dark cycle. The root initiation and shoot elongation was recorded from day 2 to 14 every 24 hours. Efficient root initiation was observed on MS basal medium only or that supplemented with ¼th nitrogen level in addition to normal concentrations. The earliest response was seen was on day 3 in the case of medium containing ¼th level of nitrogen followed by medium containing normal level of nitrogen, while in the case of zero nitrogen, initiation was observed only after 8 days. Thus, the medium with ¼ nitrogen level of standard MS basal medium was selected for root assays and was referred as MSR (rooting) medium.

In the case of the treatment with the abiotic stress factors, the plant parts/plantlets were taken into sterile petri plates or test tubes and after the treatment again inoculated into MS basal medium and incubated at 25–28° C.

The present invention is particularly described with reference to the accompanying drawings and examples which are provided to illustrate the invention and should not be considered to restrict the scope of the invention.

EXAMPLES

Example 1

To find out the effect of growth promoters such as Indole 3 acetic acid (IAA), 2,4-Dichlorophenoxy acetic acid (2,4-D), and cytokinins such as 6-Benzyl Amino Purine (6-BAP) and Kinetin, the leaf, internode and twig cuttings were inoculated into MS 0 medium containing 1 mg/ml of the above said compounds and the responses were recorded up to two weeks in terms of rooting, callusing and shoot regeneration (Table 1). This defined the typical response, which were obtained in individual examples/treatments. The unique features were aerial root formation in the case of cuttings upon auxin treatment as shown in FIG. #2 of sheet #1. On the other hand, in the case of cytokinin BAP green callus has formed, followed by shoot regeneration from leaf and internodal explant. The findings were suggestive of the use of these responses in assessing compounds for cytokinin and auxin like activities.

Table 1 summarizes the response recorded up to two weeks in terms of rooting, callusing a shoot regeneration.

TABLE 1

| Treatment | Response observed | | |
|---|---|---|---|
| | Leaf | Internode | Cutting |
| MS 0 and 2,4-D | Root Initiation Root Thickening Callus Initiation | Root Initiation Root Thickening Explant Swelling | Aerial Root Formation |
| MS 0 and IAA | Root Initiation (Profuse) | Root Initiation (Profuse) | Aerial Root Formation |
| MS 0 and BAP | Callus Initiation Shoot Regeneration | Callus Initiation Shoot Regeneration | Root Initiation Root Thickening |
| MS 0 and Kinetin | Root Initiation | No Response | Root Initiation Root Elongation |
| MS 0 only | Root Initiation Root Elongation | No response up to 15 days | Root Initiation |

Example 2

The effects of growth inhibitors were also tested using the protocol as described in Example 1. In this experiment, the twigs were in the basal MS media containing Nalidixic acid (Nal) at the rate of 10 μg/ml and 100 μg/ml and the effects were observed after 10 days of inoculation. In the case of the 10 μg ml concentration of nalidixic acid, the roots got initiated from the submerged nodes but their growth was less than the control MS basal medium. While in the case of 100 μg/ml concentration of nalidixic acid, very small roots arose from submerged node and their growth was completely arrested.

Example 3

The conditions were standardized for root tip assays to determine the effect of compounds like taxol on cell division. The following example gives the experimental procedure, which was followed and found suitable for determining cell division initiation in the roots initiated from twig cuttings of Bacopa as described in general methodology on day 7. The fresh initiated roots in MSR medium were dipped in micro-centrifuge tubes containing MS broth with solvent (DMSO or likewise), the compound (taxol dissolved in DM50 or likewise) and control (MSR broth). The dipping treatment was continued for 3 hours after which the root tips were cut and fixed in a 1:3 solution of glacial acetic acid and absolute alcohol and the fixation was continued for 24 hrs at room temperature. For long term storage such roots could be stored in 90% ethanol. For further processing these fixed roots tips were treated with 5 N HCl for 10 mm followed by thorough washing with sterile distilled water (3 to 4 times). This followed the treatment with iron alum (1%) for 30 mm and then staining with matured haemotoxylin for 2.5 hrs. The mounting was done in 45% acetic acid by gently tapping and the slide was observed under the microscope (400 to 1000 times magnification). Mitotic index was estimated based on the number of dividing cells in 10 randomly selected fields. Taxol for instance, was found to significantly reduce the mitotic index (Table 2) indicating the applicability of the procedure in detecting cell division inhibitors.

TABLE 2

| Compounds | Total No. of cells observed | Number of cells in phase | | | | Mitotic* Index |
|---|---|---|---|---|---|---|
| | | Pro | Meta | Ana | Telo | |
| 1. Control | 65 | 03 | 06 | 01 | 04 | 21.5 + 4.95 |
| 2. Taxol (10 μg/ml) | 70 | 01 | 03 | 01 | 00 | 7.14 + 1.52 |
| 3. Trichothecene - T 14-(10 μg/ml) | 37 | 03 | 00 | 00 | 00 | 8.1 + 1.45 |

*Taxol and T-14 at 100 μg/ml inhibited root initiation itself hence no mitotic index was determined.

Example 4

Simultaneously, like for the root tip assays, the procedure was also developed to determine the effect on root initiation itself by inhibitory compounds like taxol using twig cuttings. In this example, instead of pre-initiated roots, the fresh twig cuttings were directly subjected to the treatment of compound included in the rooting medium. For example, taxol was added to MSR at the rate of 1,10 and 100 μg/ml in the 0.5 ml agar medium prepared in microcentrifuge tube as described otherwise in Example 1. The treatments included compounds (taxol and likewise), solvent (DMSO and likewise) and control (plain MSR). The twig cuttings were surface sterilized and inoculated into the toxic and control media. These were then incubated as in Example 1 for root initiation and growth up to day 15. Taxol at the concentration of 10 and 100 μg/ml inhibited the complete root initiation and also had a visible effect on the aerial parts in terms of wilting of the leaves. Refer FIG. #3 of Sheet #2. The findings of this experiment further substantiated the usability of Bacopa test procedures not only for cytological parameters but also for visible phenotypic expression, for instance, root initiation and shoot health as manifested herein terms of wilting.

Example 5

To test cytotoxic effects of mint oil and other essential oils, the twigs were inoculated into the MS basal medium. Here, the mint oil was either added into the medium at the rate of 1 μl /10 ml or sprayed on the in-vitro plants at the rate of 250 μl/ml. In the case where mint oil was added into the medium, i) no root initiation was observed from the twigs, ii) wilting of twigs occurred after two days of inoculation, and iii) chlorosis occurred after 5 days. While in the case where mint oil was sprayed, i) wilting was observed on next day and ii) chlorosis recorded after 3 days of inoculation.

Example 6

In order to check the effect of radiation (Ultra Violet and gamma—Rays) on the different parts of the Bacopa plant, plantlets were exposed to Ultra Violet (UV) radiation with a 312 nm germicidal lamp from a 30 cm distance in a dark chamber for different time periods ranging from 0 hour to 12 hour and readings were recorded up to 15 days. Maximum lethality was observed in the case of total plant with overnight exposure while, in the case of the exposed plantlets with exposures of 1, 2, 4 and 8 hours, reversible lethality was observed (Table 3). It means the original plant, which was exposed to UV radiation, died but the buds were alive and later proliferated into new shoots under normal conditions. Similarly, the plantlets were exposed to gamma-radiations at 0 Kr to 100 Kr. Lethality (browning of leaf and stem tissue) was observed 15 days after exposure at the doses of 5 Kr and above. The detail data is given in the Table 4.

TABLE 3

Effect of Ultra Violet radiation on in-vitro raised Bacopa monnieri plantlets

| Dose | Lethality |
| --- | --- |
| 0 hour | − |
| 1 hour | − |
| 2 hours | + |
| 4 hours | + |
| 5 hours | + |
| 8 hours | + |
| 10 hours | + |
| over night | + |

+ = Occurred;
− = Did not occur

TABLE 4

Effect of γ - rays on in-vitro raised Bacopa monnieri plantlets.

| Dose | Shoot Proliferation | Shoot Elongation | Rooting | Lethality |
| --- | --- | --- | --- | --- |
| 0 Kr | + | 5 cm | 100% | − |
| 1 Kr | + | 5 cm | 100% | − |
| 2 Kr | + | 3 cm | 50% | − |
| 5 Kr | − | 2.5 cm | 10% | + |
| 10 Kr | − | 2 cm | − | + |
| 20 Kr | − | 1.5 cm | − | + |
| 30 Kr | − | 1.5 cm | − | + |
| 50 Kr | − | 1.5 cm | − | + |
| 100 Kr | − | 1.5 cm | − | + |

+ = Occurred
− = Did not occur

Example 7

Bacopa monnieri plant system was also used for carrying out temperature sensitivity assays by subjecting the plantlets to heat and cold shocks. Heat shocks were given at 50° C. and 80° C., and cold shock at −20 and −80° C. for varying time period ranging from 10 seconds to 30 minutes. Heat shock at 50° C. with the exposure for 3 minutes and more, killed all the plants while at 80° C. plants died after the exposure for just 20 seconds. Plants demonstrated sensitivity to cold shock of −20° C. and −80° C. within 10 minutes and 4 minutes respectively (Table 5).

TABLE 5

Temperature sensitivity of Bacopa monnieri plant

| Temperature | Time Period | | | | | | | | | | |
| --- | --- | --- | --- | --- | --- | --- | --- | --- | --- | --- | --- |
| | 10" | 20" | 30" | 1' | 2' | 3' | 4' | 5' | 10' | 20' | 30' |
| −20° C. | − | − | − | − | − | − | − | − | + | + | + |
| −80° C. | − | − | − | − | − | − | + | + | + | + | + |
| 50° C. | − | − | − | − | − | + | + | + | + | + | + |
| 80° C. | − | + | + | + | + | + | + | + | + | + | + |

" = Seconds;
' = Minutes
+ = Death of plants;
− = Plants are alive

Example 8

We also planned the experiments to determine if this procedure can depict a clear cut manifestation of cytotoxic/ weedicidal effect of compounds. For this purpose we used a known essential oil of Mentha arvensis, which is rich in the toxic but useful component, menthol as the treatment. The procedure involved was same as in the above examples with the exception that menthol was added to the medium and oil was sprayed on these twigs which were inoculated into the medium. The treatment within 3 days resulted in complete loss of chlorophyll in the lower leaves which further within a week time covered whole twig. Refer to FIG. #4 of Sheet #2. The procedure therefore, showed its use also in assessing and screening the phytotoxic chemicals.

Example 9

The above examples clearly established the use of Bacopa test procedure in detecting compounds with various biological activities such as root initiation inhibition, cell division inhibition (or anticancerous), growth promotion (shoot as well as root proliferation), growth inhibition (wilting, root stunting etc.), in vitro cell/tissue differentiation (callusing, shoot and root regeneration) and phytoxicity (Table 6). These findings were strongly supportive of accepting our test system as a unique one which by a single basic procedure can detect so many activities ranging from cytological mitotic effects to phenotypically visible plant growth parameters. We therefore, used this example to apply on various unknown and uncharacterized plant compounds and extracts just with the objective to assess the applicability of our test in a large screening program. The visible effects of these compounds established the usability of the procedure in detecting and differentiating the bioactivities of compounds.

TABLE 6

Effects of some unknown compounds on Bacopa monnieri plant

| Unknown test compound | Effect/Response | | | | |
|---|---|---|---|---|---|
| | Shoot proliferation | Root elongation | Lethality | Chlorophyll loss | Expected activity in test compound |
| A 01 | − | + | − | − | Growth promoter |
| F 01 | + | + | − | − | Growth promoter |
| 113 | − | − | + | − | Growth inhibitor |
| MRP | − | − | − | + | Cytotoxic, Weedicidal |
| Art 400 | − | − | + | + | Cytotoxic, Weedicidal |

ADVANTAGES OF THE INVENTION

The applicants used the fast propagating strain of the plant *Bacopa monnieri* for the first time to assess effect of any compound or physical factor on the responses of the plant and plant part. The system is unique because:

1. Any aerial part (internode, node, buds and leaves) can be used to initiate roots in the medium/buffer.
2. The root initiation is possible throughout the year, irrespective of the seasons, by just maintaining the temperature.
3. The initiated roots can be tested on the medium containing chemical compounds in volumes as small as 0.5 ml in microcentrifuge tubes, permitting thousands of samples to be tested in a single experiment.
4. The response of Bacopa plant or plant parts, particularly leaves, internodes and twigs, can be clearly differentiated for the auxin-like vs. Cytokinin-like activities.
5. Testing of anticancerous agents affecting the mitotic index as well as colchioine type effects can be visualized in the Bacopa test system.
6. Weedicidal/cytotoxic effect can also be detected in the Bacopa test system.
7. The response of Bacopa twigs can be used directly to assess the presence of physical factors in the environment including radioactive substances, radiations like UV/gamma-rays and sudden heat or cold shocks.
8. The usual root tip assay can be done with Bacopa in a much simpler and rapid way by initiating and monitoring the roots on the lower end of aerial twigs within 8–15 days time.

One of the studies dealing with the anatomy of the Bacopa plant is entitled *In Vitro Shoot Bud Differentiation from Epidermal Cells of Stem Segments in Bacopa monnieri* (*Linn.*) *Pennell* of Thakur et al. In this paper, the author has studied the cellular responses of the Bacopa plant to cytokinins. Thakur, et al. states that Bacopa is an ideal system for such a study, because shoot buds differentiate within 10 days. The author has observed various layers of cells in a cross section of the internode of the stem, cells observed in the cross section, the origin of shoot buds, the mitotic division, meristemoid developments, etc.

Baisi et al, (see Phytotoxicity of three antibiotics to avocado tissue culture) performed experiments in their study to verify the toxicity of nalidixic acid, chloramphenicol and streptomycin to Avocado cv. Verde in vitro. The results showed that the 3 antibiotics were toxic to avocado since the length of sprouts was reduced by the use of these antibiotics in the plant growth medium. It does not deal with biological systems for testing biotic and abiotic stress factors.

Ali et al, December, 1996 entitled "A rapid protocol for micropropagation of *Bacopa monniera* (L.) Wettset.—an important medicinal plant" printed in *Plant Tissue and Culture and Biotechnology*, Vol., No. 4, and discloses tissue culture methods to grow Bacopa and prevent its extinction. The author describes a method for micropropagation of *Bacopa monniera* (L) using nodal segments as ex-plants on MS medium in the presence of α-naphtaleneacetic acid (NAA), benzylaminopurine (BAP) and casein hydrolystate (CH). The author observed that higher amounts of BAP promoted shoot differentiation.

Ali et al 1997, entitled "Morphogenic response and isozymes of *Bacopa monniera* (L. werrst cultures grown under salt stress" printed in *Phytomorphology*, Vol 47, No. 1, Pages 97–106, is a study on the relationship between salt concentration and morphogenic response and the correlative isozyme pattern. The author proposes a protocol for the development of halophytic *Bacopa monniera* plants or salt-tolerant plants of *Bacopa monniera* (Page 105, Paragraph 1, Lines 10 and 11). Bacopa plants capable of tolerating salt levels up to 15 gm-1 were developed, by gradual exposure of the plants to increasing concentrations of salt.

Tiwari et al, 1998 entitled "Shoot regeneration and somatic embryogenesis from different explants of brahmi [*Bacopa monniera* (L.) Wettst.] printed in *Plant Cell Reports*," vol. 17, pages 538–543 (hereinafter "the Tiwari reference"), describes shoot regeneration and somatic embryogenesis using various types of ex-plants such as leaf explants, internode and node. The explants are cultured in MS medium in the presence of BAP or kinetin, allowed to form calli, from which large number of shoot buds are regenerated. Addition of Indole-3-acetic acid in the medium was found to promote shoot elongation. The elongated shoots were rooted on MS medium with or without indole-3-butyric acid or NAA. The rooted plants were then established in soil. Tiwari intended to a tissue culture method for regeneration of *Bacopa monniera* from various explants. The author suggests that the findings may be useful in micropropagation, somaclonal improvement, mutation breeding and genetic transformation of *Bacopa monniera*.

Ali et al, 1998 entitled "Effect of cadmium and copper on growth of *Bacopa monniera* regenerants" printed in *Biologi Plantaru*, Vol. 41, No. 4; Pages 635–639, determines the maximum concentration up to Bacopa cultures tolerant to aluminium can be raised (Ref. Column 2, page 240, lines 8–15). The author investigated the effect of Aluminium on the morphogenic response of Bacopa and found that Bacopa cultures could not survive beyond 400 μM of AlCl3.

The intention of Ali was to obtain aluminum tolerant bacopa plant—i.e an improved bacopa plant species so that it can be cultivated in large areas to obtain the much needed bacopa plant material for preparing various kinds of medicines.

Ali et al, 1998 entitled "Morphogenic response and Pro-line Content in *Bacopa monniera* cultures grown under copper stress" printed in *Plant Science*, Vol. 138, pages 191–195, studies the effect of cadmium and copper on in vitro growth of *Bacopa monniera*. The objective was to regenerate plants on cadmium containing medium and ascertain the extent to which copper can alleviate the toxicity of cadmium during in vitro regeneration in Bacopa (page 636, paragraph 1, lines 2–4). The study found that the regenerants of *Bacopa monniera* did not survive beyond 50,μM Cd but these could tolerate Cd up to 100 μM if grown with additional supply of Cu. The study also found that cadmium-tolerant plants can be regenerated on a medium containing cadmium and copper, and that the toxicity of cadmium can be circumvented by the addition of copper.

Ali et al, 1998 (see Morphogenic response and proline content in *Bacopa monniera* cultures grown under copper stress) discloses the in vitro response of Bacopa when subjected to copper stress at different concentrations. An appropriate supply of CuSO4 in the medium induces plant growth (Ref. Page 194, column 2, paragraph 2, lines 25–29). Thus, this investigation deals with the development of Bacopa plants which have adapted themselves to copper stress.

The cumulative effect of the teachings of these citations is either to provide tissue culture protocols or provide techniques to develop Bacopa plants tolerant to copper, aluminum, cadmium etc. It emerges from these studies that the Bacopa plant is capable of tolerating copper, aluminum, cadmium etc., up to a certain concentration and beyond the said concentration, decline in growth or similar responses are observed.

A skilled person on reading these citations would acquire enough knowledge to develop Bacopa plants from stem segments or leaf explants using tissue culture techniques. Baisi would equip the skilled person to test whether nalidixic acid and other compounds are toxic to avocado. The skilled person, even on knowing Ali 1996, Tiwari 98 and Baisi 1995 would still have no reasonable expectation that Bacopa can be used as a test system to evaluate the activity of any compound. There would be a knowledge gap between producing tissue culture techniques and evaluating the nature of a compound, whether related or unrelated to tissue culture technique, which cannot be bridged using techniques of the cited references. None of these citations would motivate a skilled person to develop a biological test system which can be used for testing abiotic and biotic stress factors. In fact, the idea behind the present invention is entirely different from the prior art which relates to improving the bacopa plant species so that it could be grown faster in areas where this plant is difficult to grow and the much needed quantum of plant material can be increased. Even by hindsight reading of the prior art, does not render the present invention obvious.

Bacopa test system is a highly sensitive plant based biosensor system which can be used in detecting the cytotoxicity of any given compounds including cell division inhibition, growth inhibition and anticancer activities.

The effects of some plant-derived compounds were tested against human cancer cell lines and Bacopa test system as described in the specification to establish the usability of this novel and unique plant biosensor system (Bacopa test) developed in the laboratory. It was observed that the compound CIM 1166 was highly effective against breast cancer cell line (MCF-7) at the concentration of 1/8000 dilution. Similarly compound 789 was effective against the oral cancer cell line (KB-403) at the concentration 1/4000 dilution. The activities of compounds on cancer cell lines were observed by drastic reduction of cell counts after the treatments. The compound CIM 1867 did not show any activity against either of the cancer cell lines used. When these compounds tested against the Bacopa test system similar results were observed. The plant compound CIM 1166 which exhibited cytotoxic properties against human breast cancer cell line MCF-7 has also shown the similar properties in the bacopa test system. This compound reduced regenerating shoot length, root length, number leaves, fresh weight and dry weight at the concentration of 50 μg/ml. Similarly the compound CIM 789 which showed cytotoxic effects against the human oral cancer cell line KB-403 exhibited similar properties the test system as described earlier. Compound CIM 1867 which was inactive against the cancer cell lines did not show any cytotoxicity as measured by observing the parameters described in the table. All these observations are given in the table below.

These observations clearly establish the usability of this plant biosensor system for determining the cytotoxic effects of any given compound in easy, quick and high throughput manner. After initial screening through this test system for these parameters one can shortlist the compounds to perform the actual test on other in vitro or in vivo systems indicating the usability of this simple method.

Table 7: The cytotoxic effect of some plant compounds on human cancer cell lines and Bacopa test system:

TABLE 7

| | Effect against cell line (MIC) | | | | | | |
|---|---|---|---|---|---|---|---|
| | MCF-7 (Breast cancer) ATCC No. HTB-22 | dKB-403 (Oral cancer) ATCC No. CCL-17 | Effect on Bacopa test system at 50 μg/ml | | | | |
| Compound | | | Shoot length (cm) | Root length (cm) | Number of leaves | Fresh weight (mg) | Dry weight (mg) |
| CIM789 | Inactive | Active (1/4000) | 2.50 | 1.25 | 10.0 | 31.50 | 7.0 |
| CIM1166 | Active (1/8000) | Inactive | 2.25 | 1.25 | 9.0 | 26.0 | 6.5 |
| CIM1867 | Inactive | Inactive | 3.20 | 1.80 | 13.0 | 73.00 | 11.5 |
| Control | | | 3.10 | 1.90 | 12.4 | 75.40 | 11.0 |

Thus the present invention provides a new assay procedure which can be used to detect a wide spectrum of activities and parameters in a single test system. This invention is also much more sensitive, fast and can test the effect of compounds of different activities in the same system, in contrast to other available individual tests. This invention can replace a number of separate tests which are now required for different compounds and activities.

The invention claimed is:

1. A method for testing bioactivity of cytotoxic compounds using *Bacopa monnieri* as a biosensor, comprising the steps of:

growing at least a part of a *Bacopa monnieri* plant aseptically in an MS 0 basal medium with agar in a microcentrifuge tube;

exposing the part of the *Bacopa monnieri* plant to a selected one of said cytotoxic compounds, wherein the cytotoxic compounds are selected from the group consisting of menthol, mint oil, artemisia oil and basil oil;

visually observing the part of the *Bacopa monnieri* plant for selected morphological and cytological responses; and in response to said step of observing the selected morphological and cytological responses, comparing the morphological and/or cytological effects of the selected compound on the exposed part against a corresponding part of a control *Bacopa monnieri* plant, thereby testing the bioactivity of cytotoxic compounds.

2. The method of claim 1, wherein said step of visually observing comprises observing the part exposed to said selected one of said cytotoxic compounds for a loss of chlorophyll over a period of 3 days immediately following said exposure.

3. The method of claim 1, wherein said step of exposing comprises the substep of adding said selected one of said cytotoxic compounds to said medium.

4. The method of claim 1, wherein said step of exposing comprises the substep of spraying the part of the *Bacopa monnieri* plant with said selected one of said cytotoxic compounds.

5. The method of claim 1, wherein said cytotoxic compounds used are either in pure or crude extract form.

6. The method of claim 1, wherein the selected morphological and cytological responses are selected from the group consisting of callus initiation, shoot induction, root induction, necrosis and death.

7. The method of claim 1, wherein the selected cytological responses are selected from the group consisting of mitotic index and C-mitosis.

8. A method for predicting and testing the effects of compounds on human cancer cells using *Bacopa monnieri* as a biosensor, comprising:

growing in a medium at least a part of a *Bacopa monnieri* plant;

exposing some portion of said *Bacopa monnieri* plant part to one or more compounds;

observing the portion of the *Bacopa monnieri* plant exposed to the one or more compounds for selected morphological and cytological responses;

comparing said observed morphological and/or cytological responses to the same morphological and/or cytological responses observed in a corresponding part of a control *Bacopa monnieri* plant not exposed to the one or more compounds to ascertain morphological and/or cytological effects of the one or more compounds; evaluating said morphological and/or cytological effects to predict effects the one or more compounds would have on human cancer cells exposed thereto as compared to similar human cancer cells not exposed thereto; and exposing human cancer cells to the one or more compounds, thereby testing the predicted effects.

9. The method of claim 8, wherein the at least a part of a *Bacopa monnieri* plant is grown aseptically in an MS 0 basal medium with agar in a microcentrifuge tube.

10. The method of claim 8, wherein at least one of the one or more compounds is selected from the group consisting of cell division inhibitors, cell growth inhibitors, and anticancer agents.

11. The method of claim 10, wherein at least one of the anticancer agents comprises a compound selected from the group consisting of taxol, tricothecene, and vincristine.

12. The method of claim 10, wherein at least one of the anticancer agents comprises a compound selected from the group consisting of CIM 1166, CIM 789, and CIM 1867.

13. The method of claim 8, wherein exposing some portion of said *Bacopa monnieri* plant part to said one or more compounds comprises contacting said plant part portion and said one or more compounds by a method selected from the group consisting of:

adding at least one of said one or more compounds to the medium;

spraying at least one of said one or more compounds onto the medium;

spraying at least one of said one or more compounds onto at least a portion of the at least a part of a *Bacopa monnieri* plant; and combinations thereof.

14. The method of claim 8, wherein observing said portion of the *Bacopa monnieri* plant exposed to said one or more compounds for selected morphological and cytological responses comprises an observation technique selected from the group consisting of:

unaided visual observation;

plant dissection;

visual magnification; and combinations thereof.

15. The method of claim 8, wherein at least one of said selected morphological and cytological responses is selected from the group consisting of:

callus initiation;

shoot induction;

root induction;

mitosis;

wilting;

necrosis;

chlorosis; and death.

16. The method of claim 15, wherein mitosis is quantified by calculating the mitotic index.

17. The method of claim 15, wherein chlorosis is established by visually observing said at least a part of a *Bacopa monnieri* plant for a loss of chlorophyll over a period of 3 days immediately following said exposure to said one or more compounds.

18. The method of claim 8, wherein said differences observed in the selected morphological and cytological responses between the *Bacopa monnieri* plant exposed to the one or more compounds and the control *Bacopa monnieri* plant part are identified by comparing at least one of the plant properties selected from the group consisting of:

shoot length;

root length;

number of leaves;

fresh weight; and dry weight.

19. The method of claim 8, wherein said human cancer cells comprise cells selected from the group consisting of:

breast cancer cell line MCF-7; and oral cancer cell line KB-153.

20. The method of claim 8, wherein the one or more compounds are present in pure or diluted form.

21. The method of claim 8, wherein the exposing of the one or more compounds to the human cancer cells comprises an exposure method selected from the group consisting of in vitro testing and in vivo testing.

* * * * *

UNITED STATES PATENT AND TRADEMARK OFFICE
CERTIFICATE OF CORRECTION

| | | |
|---|---|---|
| PATENT NO. | : 7,262,003 B2 | Page 1 of 1 |
| APPLICATION NO. | : 10/319111 | |
| DATED | : August 28, 2007 | |
| INVENTOR(S) | : Kumar et al. | |

It is certified that error appears in the above-identified patent and that said Letters Patent is hereby corrected as shown below:

Claim 19, Column 16, line 59, delete "KB-153" and insert --KB-403--;

In Table 2, Column 8, lines 36-39, delete "+" and insert --±--.

Signed and Sealed this

Twenty-fifth Day of December, 2007

JON W. DUDAS
*Director of the United States Patent and Trademark Office*